United States Patent [19]

Devlin

[11] 4,038,145
[45] July 26, 1977

[54] MALIGNANCY DIAGNOSTIC METHOD

[75] Inventor: Richard G. Devlin, Mount Vernon, Ind.

[73] Assignee: Mead Johnson & Company, Evansville, Ind.

[21] Appl. No.: 486,547

[22] Filed: July 8, 1974

[51] Int. Cl.² ............................................... C12K 9/00
[52] U.S. Cl. ................................. 195/103.5 R; 195/1.7
[58] Field of Search ........... 195/1.1, 1.4, 1.7, 103.5 R; 23/230 B

[56] References Cited

PUBLICATIONS

Gazit et al., "Mixed Leukocyte Culture with Mouse Spleen Cells in a Serum-Free Medium", Proc. Soc. Exptl. Biol & Med. 140 (1972), pp. 750-754.

Martin et al., "Derepression of Alloantigens in Malignancy", Brit. J. Cancer 28, Suppl. I, (1973), pp. 48-61.
Devlin et al., "Inhibition of Cellular Immune Reactions by Cyclophosphamide Analogues Ifosfamide and Trofosfamide", Proc. Soc. Exptl. Biol & Med. 145 (1974), pp. 389-391.

*Primary Examiner*—A. Louis Monacell
*Assistant Examiner*—C. A. Fan
*Attorney, Agent, or Firm*—R. E. Carnahan; R. H. Uloth

[57] ABSTRACT

The mixed lymphocyte reaction in tissue culture is used to detect the tumor induced autoimmune reaction which has been found to be characteristic of lymphoid malignancies. Lymphocytes from blood, spleen, and lymph nodes are employed in combinations of two. A mixed lymphocyte reaction from any one of the three possible combinations is indicative of the presence of a lymphoid malignancy.

18 Claims, No Drawings

MALIGNANCY DIAGNOSTIC METHOD

FIELD OF THE INVENTION

The present invention is in the field of immunology and involves an in vitro testing or diagnosis method employing mammalian tissue culture systems. It is based upon the discovery that mammals having lymphoid malignancies exhibit an antilymphocytic autoimmunity, that is lymphocytes from different organs in the host's body are reactive against one another as if they were foreign tissues and respond by cell division with the production of cells which are cytolytic for the lymphocytes from other organs of the host animal. Specifically it has been found that lymphocytes of the blood, spleen, and lymph nodes of mammals having lymphoid malignancies are reactive against one another in the same fashion that normal host cells are reactive against the foreign cells of a tissue graft leading to rejection. We have denominated this phenomenon tumor induced antilymphocytic autoimmune reaction (TIAAR). We have found that TIAAR can be readily measured in tissue culture by means of the mixed lymphocyte reaction employing lymphocytes from different tissues of the host's body.

DESCRIPTION OF THE PRIOR ART

The mixed lymphocyte reaction measures the afferent or cell division stage of the lymphocytic reaction of lymphoid cells in tissue culture which occurs when they are cultivated in the presence of lymphocyte reactive cells, customarily lymphoid cells from genetically different donor subjects. This is an in vitro counterpart of graft destruction which is accomplished by an immunological reaction in which the host immune lymphocytes recognize the foreign tissue (lymphocyte reactive cells) and respond by cell division (afferent phase). The cell division leads to the production of cytolytic cells which attack the foreign cells (efferent phase). Mixed lymphocyte reactions are immunologically specific. Cells of animals made tolerant to the tissue of a foreign strain fail to respond in the mixed lymphocyte reaction to cells of that strain. Tolerance induced to one strain does not affect the response to cells from a third strain in the mixed lymphocyte reaction.

The antilymphocytic response, which is the essence of the mixed lymphocyte reaction, involves an increase in cell division or preparation for cell division of the lymphocytes in response to lymphocyte reactive cells. The term "preparation for cell division" in this context refers to the synthesis of increased amounts of cellular material, particularly cellular nuclear material such as desoxyribonucleic acid, to provide genetic material and additional mass for two cells after division where only one existed before. One way to measure the response is by measuring in the increase in the number of blast cells. The classical method of identification of blast cells is staining with the dye pyronine, and thus the denomination of these cells as pyroninophilic blast cells has come into use. Direct counting is a very time consuming and cumbersome technique and other better methods are available for measuring increase in cell division or preparation for cell division.

Another method is to measure the increase in quantity of cellular material or of a cellular component material. The key component involved in cell division is desoxyribonucleic acid which is the genetic substance of the cell. Prior to cell division the quantity of desoxyribonucleic acid doubles so that each daughter cell contains identical desoxyribonucleic genetic material. Other cell constituents can be measured such as protein, certain carbohydrates, ribonucleic acid, etc. but the increase in the quantity of these components prior to the time cell division actually occurs while the cells are preparing for division is relatively less than the increase in the amount of desoxyribonucleic acid.

Direct chemical and physical analyses may be employed for cellular material or components, but the preferred method is to add a labeled cellular precursor to the culture medium and to measure the rate of incorporation thereof into the growing cells. Where the mixed lymphocyte reaction is taking place much more rapid incorporation of cellular precursors into cellular material occurs. A synergistic effect obtains in which the rate of incorporation of cellular precursors in the mixed culture is substantially greater than the sum of the incorporation of cellular precursors into the lymphocytes cultivated individually under the same conditions and in the same numbers as were combined to form the mixed culture at the outset of the assay. Various precursors which can be analyzed in cellular material are known as are various means of labeling such precursors. For instance, radioactive, fluorescent, or isotopic labeled precursors may be employed and their presence in cellular material detected by means of scintillation counting, electron spin resonance assay, chemical or photometric assay, or mass spectrographic assay.

The preferred method is to employ a radioactive pyrimidine precursor of desoxyribonucleic acid such as tritiated thymidine and to isolate the cellular material from the cultures under assay and estimate the amount of tritiated thymidine incorporated therein by scintillation counting. The precursor is added to the tissue culture medium at a predetermined time prior to harvest of the cells and the extent of preparation for cell division is reflected in the quantity of the precursor incorporated into cellular material. A culture of lymphocytes which has been challenged by contact with lymphocyte reactive cells and is undergoing preparation for cell division or actual cell division incorporates substantially greater amounts of thymidine into cell structure (desoxyribonucleic acid) as compared to a quiescent culture.

Whatever method of measurement is employed, a comparison is made between cell division or preparation for cell division of the mixed culture vs. the total of the same parameters measured for the individual cultures cultivated under the same conditions and employing at the outset the same number of lymphocytes of each tissue in the individual and mixed cultures.

The following references are representative.

Gazit and Harris, Proc. Soc. Exptl. Biol. and Med. 140, 750-754 (1972)

Devlin, Schwartz, and Baronowsky, ibid, 145, 389-391 (1974).

The mixed lymphocyte reaction has not been previously applied to detection of TIAAR. For that matter, although speculation as to the existence of TIAAR has appeared in the literature (Martin, et al., Brit. J. Cancer (1973), 28, Suppl. I, 48-61) the experiments described herein constitute the first unequivocal evidence of its existence, and for practical application thereof to diagnosis.

SUMMARY OF THE INVENTION

The present invention is applied when a mammalian subject suspected of having a lymphoid malignancy is presented for examination. The method is applicable to laboratory animals such as mice and rats, veterinary animals, such as cats and dogs, and to human beings. Lymphoid malignancies include lymphomas, leukemias, and Hodgkins Disease. Lymphocytes are separated from at least two of peripheral blood, spleen, and one or more lymph nodes of the test subject. Spleen biopsy is currently used in Hodgkins Disease diagnosis, and so a convenient source of splenic lymphocytes is readily available in that instance. The tissues are immediately transferred to a tissue culture medium in which mammilian cells of the types under consideration can be cultivated. The tissues should be kept sterile and placed in cold culture medium immediately after excision or collection. If tissue culture facilities are not immediately available, the tissues may be frozen and transported to a laboratory where such facilities are available. A sufficient sample of each tissue should be collected, for example about 100 mg. of cellular material, so that it can be readily manipulated to provide at least two culture tubes for each tissue under examination, and preferably six for each tissue since it is desirable to cultivate each culture in triplicate, each containing $3 \times 10^6$ cells. The handling of smaller quantities of tissue for tissue culture purposes according to presently available techniques leads to technical difficulties which sometimes interfere with the immunological process involved in the test. The subject under test should be free of any chemotherapeutic agent of the cytotoxic type employed for the treatment of malignancies, and should not have been subjected to X-ray treatment or other radiation therapy for a sufficient period of time previously so as to have interfered with the immunological processes involved in the test. It is preferred that the patient not have been subjected to either cytotoxic chemotherapy or radiation therapy previously and at least not within 2 weeks prior to application of the present test method. Lymphocyte cultures, preferably in triplicate, are then cultivated of each tissue individually and in combination with the other. The tissue culture tubes are incubated according to well known tissue culture techniques for a sufficient period for the mixed lymphocyte reaction to develop if lymphocyte reactive cells are present. This period can readily be determined for the specific incubation conditions employed. Ordinarily a period of 3 to 6 days is adequate. A period of 3 days after which a small amount of fresh medium containing tritiated thymidine is added to the culture medium and incubation is continued for an additional day has been found convenient and accurate. Thereafter the cells are harvested and the radioactive content thereof is determined by liquid scintillation counting employing instruments which are commerically available for this purpose. The results are interpreted by comparing the counts per minute, representing radioactive disintegration of the tritium incorporated into the growing cells, of the mixed culture with the sum of the counts per minute for the two pure cultures. A synergistic effect is observed when the mixed lymphocyte reaction occurs with the result that a substantially higher count for the mixed culture is obtained than the sum of the counts for the two pure cultures. For comparison, the ratio of the counts per minute for the mixed culture to the sum of the counts per minute of the two pure cultures is calculated. A value greater than 1 indicates that a mixed lymphocyte reaction has occurred and usually this ratio will be of the order of 2 to 30, but higher values may be obtained. Positive indication of a mixed lymphocyte reaction between spleen and lymph node lymphocytes, between spleen and blood lymphocytes, or between lymph node and blood lymphocytes taken from a patient suspected of having a lymphoid malignancy can be considered to confirm the malignancy diagnosis.

DESCRIPTION OF SPECIFIC EMBODIMENTS

Example I. Mice Bearing L1210 Leukemia

Three groups of five mice each of the DBA/2 strain and three groups of five mice each of the $BDF_1$ strain was inoculated by intraperitoneal injection with $10^5$ L1210 leukemia cells maintained by passage through $BDF_1$ mice. Between the 7th to 9th day after tumor injection, the spleens and inguinal, mediastinal, and mesenteric lymph nodes were removed from the animals. The spleens from each group of mice were combined as were the lymph nodes and the tissues were separately teased through 80 mesh screen to obtain single cells which were washed three times with RPMI 1640 medium and suspensions containing $3 \times 10^6$ cells in RPMI 1640 medium were added to culture tubes and diluted to a total volume of 3 ml. using the RPMI 1640 medium. RPMI 1640 medium is a liquid tissue culture medium developed at Roswell Park Memorial Institute and designed specifically for cultivating human and mouse leukemia cells in tissue culture (Iwakata, S., Grace, J. T., New York Journal of Medicine, 64/18:2279–2282, September 15, 1964 and Moore, G. E., Sandberg, A. A., and Ulrich, K., J. Nat. Can. Inst., 36/3:405, March, 1966). The medium has the following composition.

| Component | RPMI 1640 Medium Composition mg./l. |
| --- | --- |
| $Ca(NO_3)_2 - 4H_2O$ | 100.0 |
| Glucose | 2000.0 |
| $MgSO_4 - 7H_2O$ | 100.0 |
| KCl | 400.0 |
| $Na_2HPO_4 - 7H_2O$ | 1512.0 |
| NaCl | 6000.0 |
| L-Arginine (free base) | 200.0 |
| L-Asparagine | 50.0 |
| L-Aspartic acid | 20.0 |
| L-Cystine | 50.0 |
| L-Glutamic acid | 20.0 |
| L-Glutamine | 300.0 |
| Glutathione (reduced) | 1.0 |
| Glycine | 10.0 |
| L-Histidine (free base) | 15.0 |
| L-Hydroxyproline | 20.0 |
| L-Isoleucine (Allo free) | 50.0 |
| L-Leucine (Methionine free) | 50.0 |
| L-Lysine HCl | 40.0 |
| L-Methionine | 15.0 |
| L-Phenylalanine | 15.0 |
| L-Proline (Hydroxy L-Proline free) | 20.0 |
| L-Serine | 30.0 |
| L-Threonine (Allo free) | 20.0 |
| L-Tryptophan | 5.0 |
| L-Tyrosine | 20.0 |
| L-Valine | 20.0 |
| Biotin | 0.2 |
| Vitamin $B_{12}$ | 0.005 |
| D-Calcium pantothenate | 0.25 |
| Choline Cl | 3.0 |
| Folic acid | 1.0 |
| i-Inositol | 35.0 |
| Nicotinamide | 1.0 |
| Para-Aminobenzoic acid | 1.0 |
| Pyridoxine HCl | 1.0 |
| Riboflavin | 0.2 |
| Thiamine HCl | 1.0 |
| Phenol red | 5.0 |
| $NaHCO_3$ | 2000.0 |

In addition to the foregoing, penicillin, 50 units/ml.; streptomycin, 50 mcg./ml.; and L-glutamine, 1 ml. of 200 mM solution per 100 ml. of medium were included in the composition. The cultures were set up in triplicate in plastic culture tubes which stood in a vertical position in a humidified 37° C. incubator containing an atmosphere of 95% air and 5% carbon dioxide. After 3 days, 1 ml. of fresh medium containing 1 $\mu$Ci/ml. of tritiated thymidine was added to each culture tube; 18–24 hrs. later the cells were harvested by centrifugation. They were then treated with 0.5 ml. of 1% horse serum and with cold 5% trichloroacetic acid for one hour. They were centrifuged and treated an additional two times with cold 5% trichloroacetic acid and centrifugation. The residue was dissolved in a toluene solution of methylbenzethonium chloride and diluted with a liquid scintillation counting solution containing 4 g./l. of 2,5-diphenyloxazole and 50 mg./l. of p-bis-[2-(5-phenyloxazolyl]benzene. The tritium decompositions were counted in a liquid scintillation counter. Each grouped tissue specimen was cultivated and counted separately, and mixed cultures of spleens and lymph nodes from the same groups of animals were also cultivated and counted. The results of the experiments are tabulated in the following table. In this table for each experiment the counts as DPM (disintegrations per minute) for each tissue specimen and for the pairs thereof cultivated in mixed culture are tabulated. The latter values are listed in the column entitled "MLR" which refers to mixed lymphocyte reaction. The results are summarized in the right-hand most two columns in which the combination of tissues tested for mixed lymphocyte reaction and the ratio (R) of the DPM for the mixed culture as compared to the total DPM for the two individual cultures is reported. A value greater than 1 for R signifies a reaction of the cultured tissues against one another or of one against the other since an abnormal degree of cell division or preparation for cell division is signified by the increased DPM. It is evident that in both the DBA/2 and BDF$_1$ strains of mouse that lymphocytes of the spleen and of the lymph nodes of mice bearing the L1210 leukemia are reactive while in normal animals no reaction occurs between the lymphocytes of the spleen and lymph node.

Example II. Mice Bearing P388 Leukemia

The mixed lymphocyte reaction between spleen and lymph node is also observed when mice inoculated with P388 leukemia are grown and tissue specimens evaluated as described in Example I.

Example III. Lymphoma in Mice

Mice are inoculated with lymphoma cells. After development of the malignancy, tissue specimens of spleen and lymph node are taken and evaluated for mixed lymphocyte reaction as described in Example I.

In man, tissue culture techniques for conducting the mixed lymphocyte reaction employing lymphocytes isolated from the peripheral blood of proposed donors and recipients of kidney transplants have been standardized. The same technique is applicable to the present invention employing lymphocytes isolated from the peripheral blood, from the spleen, or from a lymph node in any combination of two of a patient suspected of having a lymphoid malignancy such as Hodgkins Disease or leukemia. The development of a mixed lymphocyte reaction with any combination of two of these tissues (i.e., lymph node and spleen, lymph node and blood, or spleen and blood) signifies the presence of an autoimmune condition which occurs in subjects having lymphoid malignancies.

What is claimed is:

1. The method for diagnosing lymphoid malignancy in a mammal employing the mixed lymphocyte reaction in tissue culture which comprises securing tissue specimens from at least one pair of tissues selected from the group consisting of lymph node, spleen, and blood of said mammal, individually preparing single cell suspensions of lymphocytes contained in said specimens in an aqueous tissue culture medium in which said lymphocytes can be cultivated, cultivating said lymphocytes of at least one pair of said tissues separately and together as a mixed culture in said medium for a period sufficient for the development of the mixed lymphocyte reaction when lymphocyte reactive cells are present, and determining whether a mixed lymphocyte reaction has occurred.

2. The method of claim 1 wherein said pair of tissues consists of spleen and lymph node.

3. The method of claim 1 wherein said pair of tissues consists of spleen and blood.

4. The method of claim 1 wherein said pair of tissues consists of lymph node and blood.

5. The method of claim 1 wherein said lymphoid malignancy is Hodgkins Disease.

6. The method of claim 1 wherein said lymphoid malignancy is leukemia.

7. The method of claim 1 wherein said lymphoid malignancy is a lymphoma.

MIXED LYMPHOCYTE REACTIONS OF SPLENIC AND LYMPH NODE LYMPHOCYTES OBTAINED FROM GROUPS OF FIVE MICE

| Experiment # | Strain | DPM Spleen | DPM Lymph Node | MLR | Combination | R[1] |
|---|---|---|---|---|---|---|
| 22 | DBA/2 | 20,986 | 153 | 378,219 | Tumor Spleen[2] × Tumor Lymph Node[2] | 17.9 |
| 101 | DBA/2 | 6,200 | 242 | 36,215 | Tumor Spleen[2] × Tumor Lymph Node[2] | 5.6 |
| 100 | BDF$_1$ | 8,434 | 4,979 | 365,635 | Tumor Spleen[2] × Tumor Lymph Node[2] | 27.3 |
| 18 | BDF$_1$ | 11,094 | 74 | 26,666 | Tumor Spleen[2] × Tumor Lymph Node[2] | 2.4 |
| 105 | DBA/2 | 1,222 | 385 | 431 | Normal Spleen[3] × Normal Lymph Node[3] | <1 |
| 19 | BDF$_1$ | 612 | 91 | 80 | Normal Spleen[3] × Normal Lymph Node[3] | <1 |

[1] Counts in mixed cultures (MLR) divided by sum of counts in cultures of each cell type separately.
[2] Spleen and lymph nodes taken from mice bearing the L1210 leukemia.
[3] Spleen and lymph nodes taken from normal mice.

8. The method of claim 1 wherein said mammal is a human being.

9. The method of claim 1 wherein said mammal is a veterinary animal.

10. The method of claim 1 wherein said mammal is a laboratory animal.

11. The method of claim 1 wherein said mixed lymphocyte reaction is determined by comparing the numbers of blast cells formed in said mixed culture to the total numbers of blast cells formed in individual cultures of lymphocytes of said pair of tissues constituting said mixed culture when cultivated separately under the same conditions as said mixed culture, each of said individual cultures containing at the outset like numbers of the individual lymphocytes as were contained in said mixed culture at the outset.

12. The method of claim 1 wherein said mixed lymphocyte reaction is determined by comparing the quantity of cellular material formed by said mixed culture to the total quantity of cellular material formed in individual cultures of lymphocytes of said pair of tissues constituting said mixed culture when cultivated separately under the same conditions as said mixed culture, each of said individual cultures containing at the outset like numbers of the individual lymphocytes as were contained in said mixed culture at the outset.

13. The method of claim 12 wherein said cellular material is desoxyribonucleic acid.

14. The method of claim 12 wherein a labeled cellular precursor substance is added to each of said individual cultures and to said mixed culture, and the rate of incorporation of said labeled cellular material, into lymphocyte cells of each of said individual cultures and said mixed culture is determined.

15. The method of claim 13 wherein said labeled cellular precursor is radioactive.

16. The method of claim 13 wherein said labeled cellular precursor is a precursor of desoxyribonucleic acid.

17. The method of claim 13 wherein said labeled cellular precursor is tritiated thymidine.

18. The method for diagnosing lymphoid malignancy in a mammal by means of the mixed lymphocyte reaction in tissue culture which comprises securing tissue specimens from at least one pair of tissues selected from the group consisting of lymph node, spleen, and blood of said mammal and determining whether antilymphocytic autoimmune reactivity exists between the lymphocytes of said pair of tissues when grown separately and as a mixed culture in tissue culture by means of the mixed lymphocyte reaction.

* * * * *